United States Patent [19]
Herr et al.

[11] Patent Number: 5,701,686
[45] Date of Patent: Dec. 30, 1997

[54] SHOE AND FOOT PROSTHESIS WITH BENDING BEAM SPRING STRUCTURES

[76] Inventors: Hugh M. Herr, 20 Daniels St., Apt. 222, Malden, Mass. 02148; Rustem Igor Gamow, 9 Canyon Park, Boulder, Colo. 80302

[21] Appl. No.: 346,087

[22] Filed: Nov. 29, 1994

Related U.S. Application Data

[63] Continuation-in-part of Ser. No. 222,717, Apr. 4, 1994, abandoned, Ser. No. 47,872, Apr. 15, 1993, Pat. No. 5,367,790, and Ser. No. 726,891, Jul. 8, 1991, abandoned.

[51] Int. Cl.⁶ ................................. A43B 13/28
[52] U.S. Cl. ................................. 36/27; 36/7.8
[58] Field of Search ................ 36/7.8, 27, 38, 36/37; 623/55

[56] References Cited

U.S. PATENT DOCUMENTS

| Re. 9,618 | 3/1881 | Nichols | 36/27 |
|---|---|---|---|
| 324,065 | 8/1885 | Andrews | 36/37 |
| 427,136 | 5/1890 | Walker | 36/7.8 X |
| 1,022,672 | 4/1912 | Hammer | 36/37 X |
| 4,492,046 | 1/1985 | Kosova | 36/27 |
| 4,771,554 | 9/1988 | Hannemann | 36/27 |
| 5,138,776 | 8/1992 | Levin | 36/38 |
| 5,367,790 | 11/1994 | Ganow et al. | 36/27 |

FOREIGN PATENT DOCUMENTS

| 2507066 | 12/1982 | France | 36/27 |
|---|---|---|---|
| 608180 | 9/1948 | United Kingdom . | |
| 2200030 | 7/1988 | United Kingdom | 36/27 |
| US95/15570 | 11/1995 | WIPO . | |

*Primary Examiner*—Ted Kavanaugh
*Attorney, Agent, or Firm*—Greenlee, Winner, and Sullivan, P.C.

[57] ABSTRACT

Bending beam sole systems for shoes or foot prostheses comprising a bending beam heel spring, a bending beam forefoot spring, a two coupled spring sole system, and a three coupled spring sole system. The sole systems of this invention maximize stability, cushioning, and walking or running economy.

4 Claims, 13 Drawing Sheets

SHOE AND FOOT PROSTHESIS WITH BENDING BEAM SPRING STRUCTURES

CROSS-REFERENCE TO RELATED APPLICATIONS

This application is a continuation-in-part of U.S. Ser. No. 08/222,717 filed Apr. 4, 1994 now abandoned, a continuation-in-part of allowed U.S. Ser. No. 047,872 filed Apr. 15, 1993 now U.S. Pat. No. 5,387,790, a continuation of U.S. Ser. No. 07/726,891 filed Jul. 8, 1991, now abandoned. Said prior applications are incorporated by reference herein in their entirety.

TECHNICAL FIELD

The invention relates to spring systems for use especially with a shoe or foot prosthesis. The spring systems include a bending beam heel spring, a bending beam forefoot spring, a two-coupled-spring bending beam configuration, and a three-coupled-spring bending beam configuration. Each spring system is designed to behave optimally biomechanically and structurally within a shoe sole or foot prosthesis.

BACKGROUND OF THE INVENTION

Developers of elastic shoe soles are confronted with the problem of storing energy in the sole of the shoe and releasing the energy in a manner which improves walking and running economy while at the same time achieving adequate shoe stability and cushioning.

Proposed spring designs for shoe soles have not been entirely satisfactory. The spring structures are not optimally light and efficient while still meeting biomechanical stiffness and stability requirements. These problems are overcome by the present invention. The inventors hereof have designed an optimal heel spring and forefoot spring. In addition, the inventors hereof have discovered that for heel-toe running, energy should be stored in the sole of the shoe at heel-strike and then, in turn, this stored energy should be released at a critical time and in a particular manner to enhance toe-off propulsion. A two and three coupled spring system was designed which achieves this heel to toe transfer of energy.

While purporting to provide for maximum performance, the latest technology in elastic shoe soles fails to achieve the ultimate design which permits maximum storage and return of energy while still achieving shoe stability and cushioning in a variety of locomotion modes ranging from heel-toe walking and running, flat-footed running (long-distance) and toe running (sprinting).

U.S. Pat. No. 4,941,273 (Gross) discloses an athletic shoe having a sole arrangement which contains an elastic band extending through a longitudinal passageway in the midsole. The purpose of this device is to create an artificial tendon which stores and releases energy during the running cycle. However, this heel spring design is inadequate for several reasons. Most importantly, the spring stiffness does not increase with increasing running speed, an essential heel spring performance requirement.

On the other hand U.S. Pat. No. 4,492,046 (Kosova) describes a sole of a running shoe having a wire spring. The wire spring serves to bias the anterior portion of the sole from the heel (back of shoe) forward to the arch region, separating the anterior of the sole into upper and lower portions. The objective of this device is to enhance the runner's performance by reducing impact at heel-strike and launching the runner forward into a comfortable stride. Unfortunately, this wire spring configuration could not be optimally light while at the same time adequately stiff for both running and walking. Additional material would have to be used within the wire frame to achieve adequate heel stiffnesses. This additional material would most likely reduce the overall heel spring efficiency.

The latest commercially available elastic shoes fail to completely address the desired attributes of a properly designed shoe with springs. For example, air bladders have been used in shoe soles in an attempt to increase walking and running economy. Researcher have found that it is difficult to achieve shoe stability while simultaneously achieving measurable increases in economy using air springs. Other commercially available shoes, although claiming to facilitate propulsion at toe-off, are incapable of storing substantial amounts of energy at heel-strike, allowing kinetic and potential energies to be lost to heat.

Similar challenges have confronted developers of lower-extremity prosthetic limbs. While it has effected substantial improvements, prosthetic research has so far focused almost exclusively on simulation or duplication of a natural foot in an attempt to provide the amputee with a normal gait and a greater degree of comfort. See U.S. Pat. No. 4,652,266 (Truesdell). A recent improvement emerging from research is the College Park Foot design disclosed in U.S. Pat. No. 4,892,554 (Robbinson). This design describes a prosthetic foot having an ankle member, a heel member and an elongated metatarsal-toe member coupled to each other for relative pivotal movements. The toe member is partially bifurcated at its forward end to provide independently flexible toe sections at the inner and outer sides of the foot. This design thus represents a three-point balance system achieving a stable support matching that of a natural foot.

One notable exception is the device disclosed in U.S. Pat. No. 4,822,363 (Phillips). This patent describes a composite prosthetic foot having a leg portion, a foot portion and a heel portion all rigidly joined and all three provided with substantial elasticity to allow return of energy absorbed and permit the amputee to engage in sports such as running and playing tennis. Understandably, this design has met with general approval from amputees who are sport enthusiasts, and at the same time enjoyed commercial success.

The above disclosed invention does not contain a mechanism whereby energy absorbed at heel-strike can be stored and later released at toe-off as does the two and three coupled spring systems disclosed herein.

SUMMARY OF THE INVENTION

This invention comprises optimally designed heel and forefoot spring structures for absorbing the energy of impact of the heel and forefoot against a surface, respectively. During foot contact in walking and running, the stored energy in the heel and forefoot springs is released to enhance heel and forefoot lift-off from said surface, respectively. In addition, this invention comprises coupled spring sole systems for absorbing the energy of impact of the heel of the foot against a surface and releasing said energy after sufficient delay to allow said foot to roll forward, whereby said released energy provides a horizontal and vertical component of force to the front portion of said foot to enhance forward lift of said foot.

This invention demonstrates how efficient springs can be used in walking and running shoe soles and prosthetic feet to maximize shoe or prosthetic foot cushioning, stability and efficiency. The term "spring" as used in this document is defined as follows. When forces compress, bend, or stretch a body, the body is said to be a "spring" if it returns to its original shape after the forces are released. The body is considered an "efficient spring" if 70% or more of the work done to deform the body can be performed by the body itself as it returns to its original shape, i.e. the spring provides 70% energy return. An energy return of 90% or higher is preferred for the heel, forefoot, and coupled spring structures described in this document. To attain this, the present invention provides spring structures made of suitable energy-absorbing material, e.g., a carbon fiber composite or other suitable materials known to the art having non-plastic properties.

The coupled springs may consist of a plurality (two or more) of springs positioned with respect to each other such that energy absorbed by a first spring or springs is transferred to one or more additional springs and released by said additional spring or springs. The first spring or springs are positioned beneath the foot so as to absorb energy from impact of the foot against a surface (referred to herein as "heel-strike"), and release the absorbed energy in such a way as to allow at least a portion of energy to be absorbed by second spring or springs. Said second spring or springs release the energy against the underside of the front portion of the foot, i.e., at or near the ball of the foot to provide both an upward and a forward component of force to propel the foot forward and upward (referred to herein as "toe-off"). In addition a forefoot spring begins to store energy when the forefoot strikes the running surface and continues to compress as the center of pressure moves into the forefoot region. Expansion of the forefoot spring enhances toe-off propulsion.

By this arrangement sufficient delay is provided between absorption of energy from the heel-strike and release of energy back to the front part of the foot to allow the foot to roll forward in a normal walking or running gait before the energy is released to enhance toe-off propulsion.

The first embodiment of the sole system of this invention comprises a heel spring formed by upper and lower bending beams. The bending beams are coupled together near the fore end of the heel spring. By definition, the fore end of a spring structure is closer to the front end or toe end of a shoe or foot prosthesis than its aft end whereas the aft end is closer to the heel end of a shoe or foot prosthesis than its fore end. The heel spring is positioned beneath the human foot between the heel and the metatarsal-phalangeal (M-P) joints, also called the ball-of-the-foot joint, approximately, in a shoe, and in an analogous position in a foot prosthesis. As will be apparent, the aft end of the heel spring must extend far enough toward the heel to be compressed at heel strike, and the fore end must not extend so far forward as to interfere with flexing of the ball-of-the-foot joint.

A bending beam axis is formed where the bending beams first adjoin. The coupled region is located between the bending beam axis and the heel spring's fore end. When the heel spring is compressed by an outside agent, the bending beams bend toward one another and store energy. The curvature and tapering of the various heel spring sections is critical to the biomechanical and structural performance of the heel spring. These design details will be fully described in the next section.

During a heel-toe walking or running sequence, the heel spring begins to compress and store energy when the heel strikes the ground. As the foot rolls forward, the compressed spring expands, thrusting the heel upwards away from the ground. During foot contact in running and walking, the heel spring can reduce impact forces, minimize ankle pronation for shoe sole applications, and store energy if designed properly.

The second embodiment of the sole system of this invention comprises a sole spring coupled to a heel spring. The sole spring is a bending beam with a bending axis located approximately ⅔ of the sole system length from its aft end. In a shoe sole, the sole spring bends about this axis and stores energy when the foot flexes about the metatarsal-phalangeal joints commonly referred to as the ball of the foot joint. In a prosthetic foot, the bending of the sole spring about this axis simulates natural metatarsal-phalangeal joint flexion. The heel spring, formed by upper and lower bending beams as described earlier, is coupled to the sole spring such that the bending beam axis is positioned between the aft end of the sole system and the sole spring axis. The word "coupled" does not necessarily mean rigidly attached. If two parts are coupled together, a force exerted on one will influence the other. This does not require the parts to be rigidly attached.

During a heel-toe walking or running sequence, the heel spring compresses and stores energy as the heel of the shoe or prosthesis strikes the ground. In a shoe sole, the compressed heel spring then exerts a force underneath the user's heel, thrusting the heel upward as the foot flexes about the metatarsal-phalangeal joints. During this flexion period, the sole spring compresses about the sole spring axis and stores energy. The spring exerts a torque about the metatarsal-phalangeal joints, enhancing toe-off propulsion. In a prosthetic foot, the expansion of the heel spring enables the amputee to bend the sole spring about its sole spring axis. The sole spring energy then gives the amputee toe-off propulsion. Thus, effectively the elastic energy stored at impact is transferred to the sole spring. Elastic energy is stored in the sole system early in the foot contact period and then released to the user late in the period to enhance or create toe-off propulsion. This method of delivering the heel spring energy to the walker or runner is believed to be optimal.

A third embodiment of the sole system of this invention consists of a forefoot spring formed by upper and lower bending beams. The bending beams are coupled together near the fore end of the spring. The forefoot spring is positioned such that when the user puts weight on the toes, the spring compresses. The spring is positioned beneath the human foot between the user's toes (fore end of the human foot) and the M-P (ball-of-the-foot) joint, approximately, and in an analogous location in a foot prosthesis. A bending beam axis is formed where the bending beams first adjoin. The coupled region is located between the bending beam axis and the forefoot spring's fore end. When the forefoot spring is compressed by an outside agent, the bending beams bend toward one another and store energy. The curvature and tapering of the various spring sections is critical to the biomechanical and structural performance of the forefoot spring. These design details will be fully described in the next section.

During foot contact in walking and running, the forefoot spring begins to compress and store energy when the forefoot of the shoe or prosthesis strikes the ground. In a shoe sole, as the metatarsal-phalangeal joints begin to extend during toe-off propulsion, the compressed spring expands, thrusting the forefoot upwards away from the ground. In a prosthetic foot, the compressed forefoot spring expands, thrusting the prosthetic foot away from the ground. The forefoot spring can reduce impact forces, minimize ankle supination in shoes, and store energy if designed properly.

A fourth embodiment of the sole system of this invention consists of a sole system comprising three coupled springs: a heel spring, a sole spring, and a forefoot spring. As described earlier, the sole spring is a bending beam with a bending axis located approximately ⅔ of the sole system length from its aft end. In a shoe sole, the sole spring bends about this axis and stores energy when the foot flexes about the metatarsal-phalangeal joints commonly referred to as the ball of the foot joint. In a prosthetic foot, the bending of the sole spring about this axis simulates natural metatarsal-phalangeal joint flexion. The heel spring, formed by upper and lower bending beams as described earlier, is coupled to the sole spring such that the bending beam axis is positioned between the aft end of the sole system and the sole spring axis. The forefoot spring, formed by upper and lower bending beams as described earlier, is coupled to the sole spring such that the bending beam axis is positioned between the fore end of the sole system and the sole spring axis. Again, the word "coupled" does not necessarily mean rigidly attached, or even touching. If two parts are coupled together, a force exerted on one will influence the other. This does not require the parts to be rigidly attached.

When the heel of a shoe or foot prosthesis strikes the ground during a heel-toe walking or running sequence, the heel spring compresses and stores energy. After heel impact, the forefoot of the shoe or foot prosthesis strikes the ground and the forefoot spring begins to compress. The forefoot spring continues to compress as the center of pressure moves into the forefoot region. The shifting of weight from the heel to the forefoot enables the heel spring to release its energy, propelling the heel upward away from the ground. The heel spring energy helps to bend the sole spring as discussed earlier. After this bending period, forefoot lift-off begins. The forefoot spring begins to release its energy pushing on the bottom of the forefoot. During the same period, the sole spring releases its energy creating or enhancing toe-off propulsion. Thus, during this final period, both the sole spring and the forefoot spring release energy propelling the walker or runner upwards and forwards.

Each of the four embodiments described herein have advantages and disadvantages over the other three with regard to biomechanical performance, structural performance, or manufacturing cost performance. For example, the three coupled spring sole system is biomechanically superior to the two coupled spring sole system, and the two coupled spring sole system is superior to the bending beam heel spring sole system. However, the three coupled spring sole system is more costly to manufacture than the two coupled spring sole system, and the two coupled spring sole system is more costly than the bending beam heel spring sole system. Each bending beam sole system described herein has been designed to meet a specific need in the shoe or prosthetic foot market place.

All embodiments of spring sole systems could be either permanently glued into the sole of a shoe, or the sole systems could be part of modular shoes where the springs snap into or out of a shoe sole. In addition, the springs could be attached to the bottom of a conventional shoe using straps or the like, or to the bottom of an orthotic brace shoe. Still further, the springs could be used as part of a prosthetic foot with the springs placed inside a cosmetic foot cover.

The exact nature of this invention as well as other objects and advantages thereof will be readily apparent from consideration of the following specification related to the drawings.

DETAILED DESCRIPTION OF THE PREFERRED EMBODIMENTS

The first embodiment of this invention is a heel spring. During a heel-toe walking or running sequence, a heel spring begins to compress and store energy as the heel of the shoe or foot prosthesis strikes the ground. During this period, a heel spring can reduce impact forces, minimize ankle pronation in shoes, and store energy if designed properly.

Figure 1:
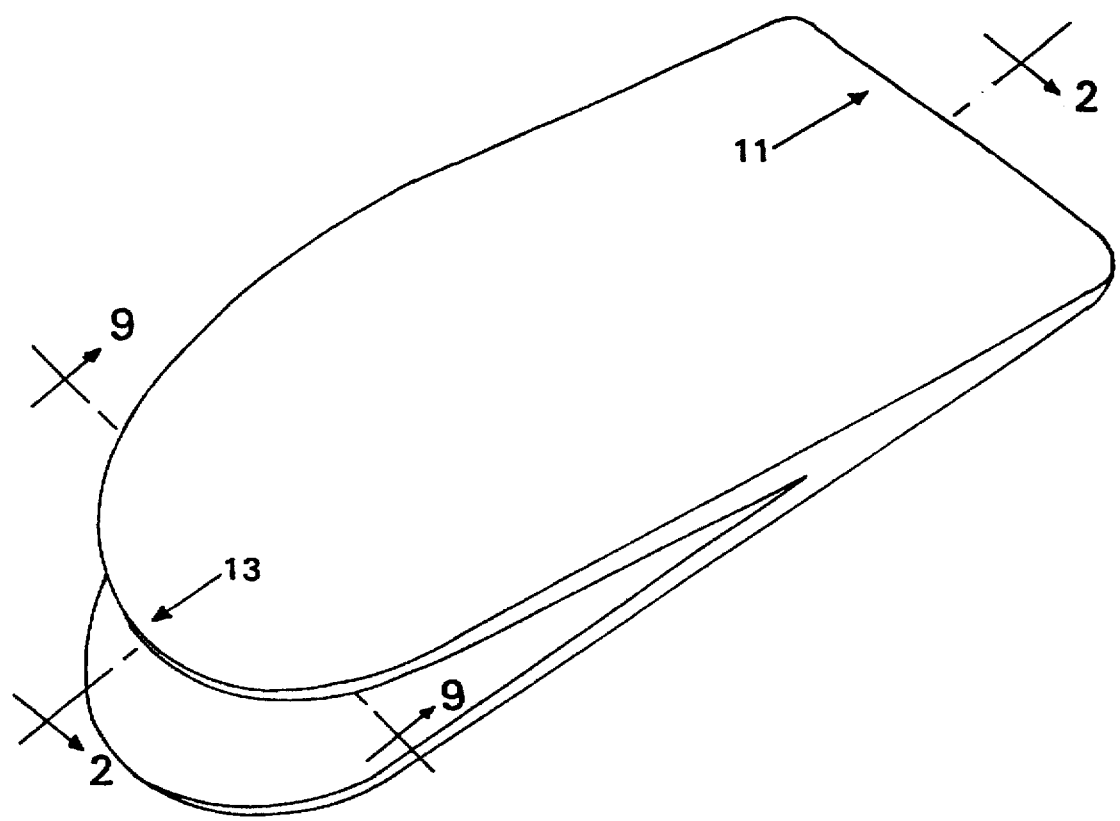
FIG. 1 shows a perspective view of a bending beam heel spring.
Figure 2:
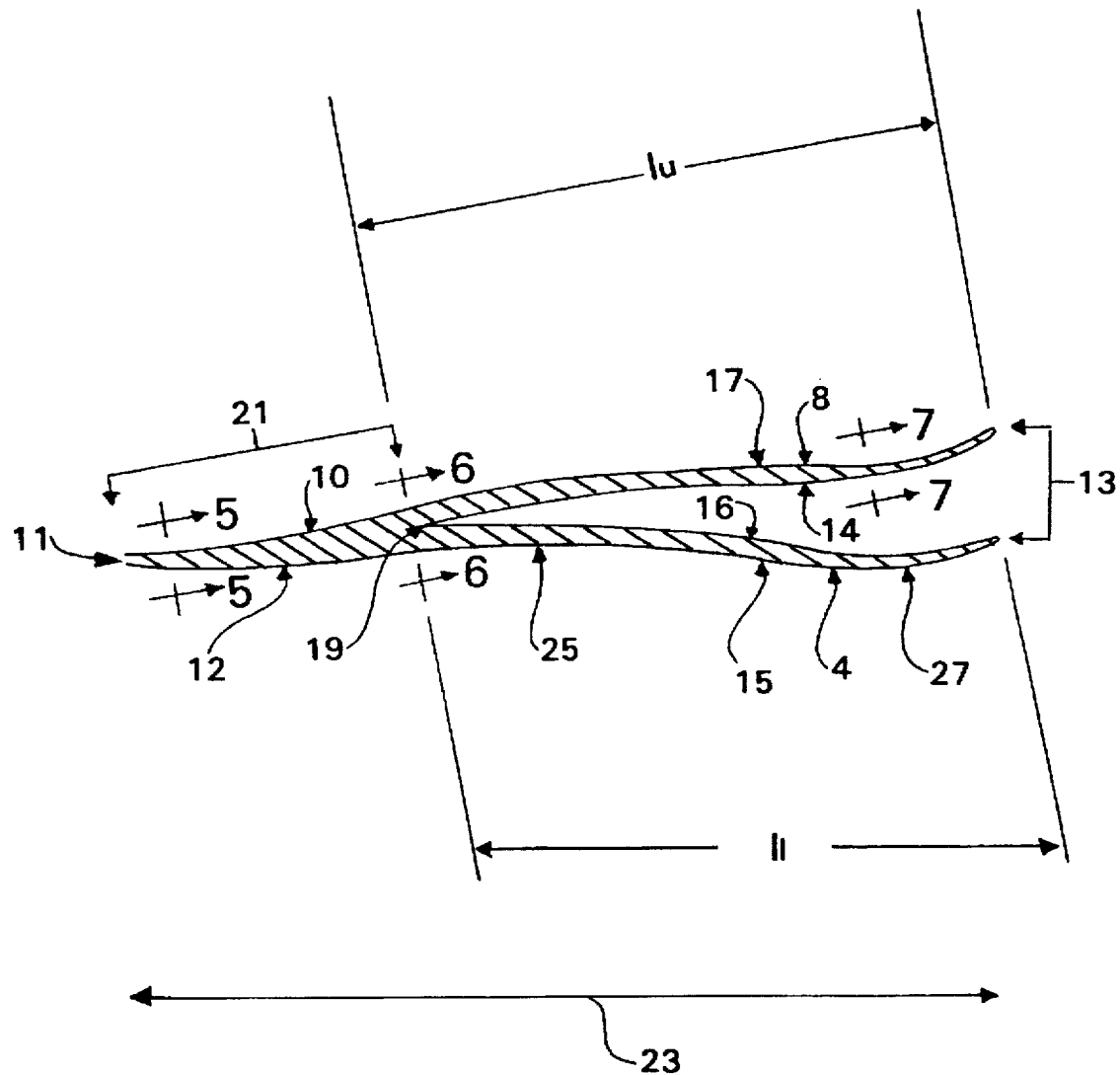
FIG. 2 shows a sectional view taken on the line 2—2 in FIG. 1.

In FIG. 1, a perspective view of an optimized heel spring is sketched. In FIG. 2, the sagittal plane cross sectional view (line 2—2 in FIG. 1) taken through the approximate heel spring center line is shown. The spring has a fore end 11 and an aft end 13. Relative to the foot of the shoe user, the spring's aft end 13 would be closer to the user's heel than the spring's fore end 11, and the spring's fore end 11 would be closer to the user's toes than the spring's aft end 13. Two bending beams, an upper beam 17 and a lower beam 15, form the spring. When the heel spring is compressed by an outside agent, the bending beams 15 and 17 bend towards each other and store energy. The transverse axis where the bending beams come together will be referred to as the bending beam axis 19. Bending beams 15 and 17 are coupled together at and near the fore end 11 of the heel spring. The region where the beams are adjoined will be referred to as the coupled region 21.

The geometries of the bending beam heel spring are critical to the spring's performance structurally and biomechanically. The first feature of interest is the curvature of the bending beams 15 and 17 in the fore and aft directions defined by axis 23 of FIG. 2. In FIG. 2, the heel spring is sketched without the bending beams compressed or distorted by an outside agent in anyway; the spring is sketched in its natural equilibrium state. The curvature of each bending beam changes concavity. Arrows 15 and 17 point to the locations where the lower and upper beam curvatures change concavity, respectively. Between these points of concavity change and the bending beam axis 19 each beam is concave downwards. These beam sections will be referred to as the concave downwards regions; the top and bottom surfaces of these beam sections form continuous concave downwards lines in the fore and aft directions 23 in FIG. 2. Between each beam's point of concavity change and its aft end, the curvature is concave upwards. These beam sections will be referred to as the concave upwards regions; the top and bottom surfaces of these beam sections form continuous concave upwards lines in the fore and aft directions 23 in FIG. 2. For the lower beam's lower surface 4, arrow 27 points to the beam section where the radius of curvature is smallest in the concave upwards region, and arrow 25 points to the beam section where the radius of curvature is smallest in the concave downwards region. For each beam, the minimum radius of curvature in the concave upwards region is less than the minimum radius of curvature in the concave downwards region.

The second feature of interest is the curvature of coupled region 21 in the fore and aft directions defined by axis 23 in FIG. 2. Coupled region 21 does not change concavity and is concave upwards; the top and bottom surfaces of coupled region 21 form continuous concave upwards lines in the fore and aft directions in FIG. 2.

Figure 3:
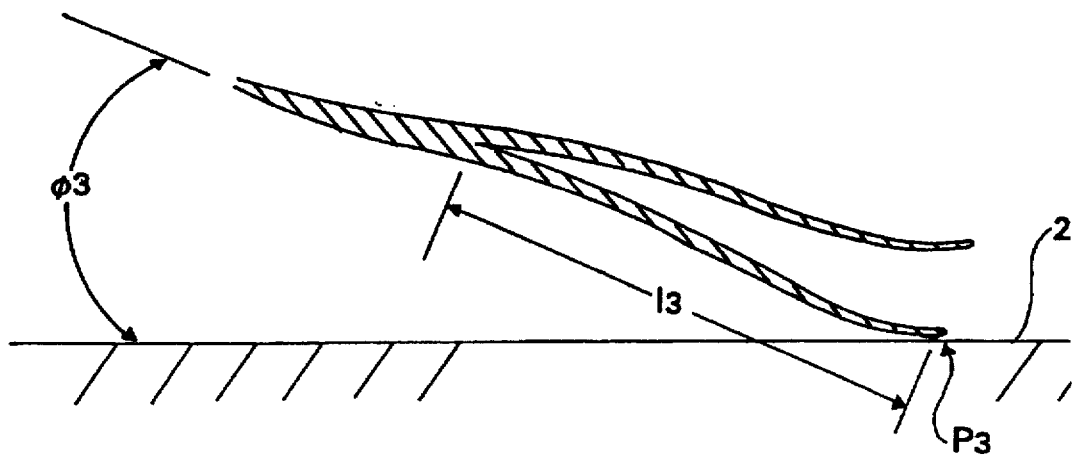
FIG. 3 shows a sectional view taken on the line 2—2 in FIG. 1 with the device tilted up at an angle from the ground.
Figure 4:
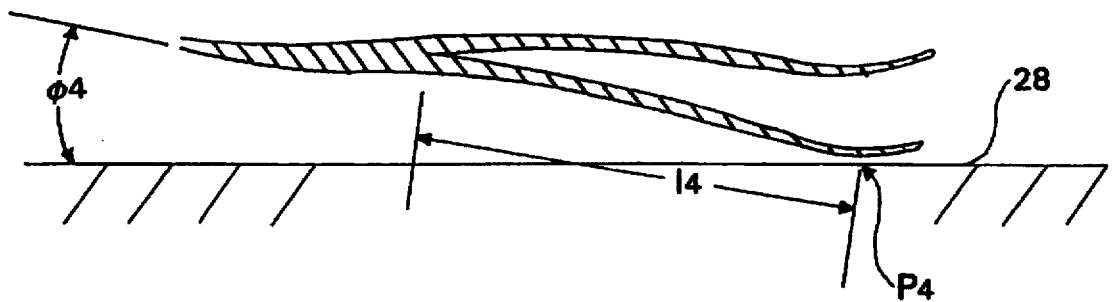
FIG. 4 shows the same view as in FIG. 3 except the angle between the heel spring and the ground is reduced.

Bending beam and coupled region curvature is critical to the performance of the heel spring for several reasons. The upper continuous surface of the heel spring formed by the upper surface 8 of upper beam 17 and the upper surface 10 of coupled region 21 fits nicely to the underside of a shoe user's foot. The shoe user's heel fits into the concave upwards region of the upper surface 8 of upper bending beam 17, and the concave downwards regions of the upper bending beam's upper surface 8 and coupled region's upper surface 10 follow the natural curvature of the shoe user's arch. Thus, the curvature of the upper surface of upper beam 8 is more critical than that of the upper beam's lower surface 14, and the curvature of the upper surface of coupled region 10 is more critical than that of the coupled region's lower surface 12. The curvature of the lower beam 15 is even more critical. As the spring is compressed, the top and bottom beams bend towards one another and store energy. The normal forces required to compress the bending beams towards one another a unit distance are less when the compressive forces act at large bending beam moment arms compared to smaller moment arms. The bending beam moment arm is defined as the distance from the bending beam axis 19 to the point of force application (distance lu in FIG. 2 is the largest possible upper bending beam moment arm). The fact that the spring is more difficult to compress closer to the bending beam axis 19 and that the lower bending beam 15 has a concave upwards region is important for walking and running. As a person changes speed from walking to running, the peak vertical ground reaction force increases. (When the foot is in contact with the ground in walking or running, the foot pushes on the ground, and the ground pushes against the foot. The latter is the ground reaction force. The component of this ground reaction force vector in the vertical direction is the "vertical ground reaction force.") In addition, as shown in FIGS. 3 and 4, the angle between the bottom of the foot and the running surface at the instant of first foot contact decreases as speed increases. Thus, as speed increases, the lower bending beam moment arm at first foot contact decreases due to a rolling effect of the concave upwards region on the ground. The reduction in moment arm increases the required force to compress the bending beams a unit distance, stiffening the heel spring at higher locomotion speeds. In FIG. 3, the sagittal plane cross-sectional view of the heel spring is sketched with the angle between the ground 28 and the heel spring at $\phi 3$ and a lower bending beam moment arm at 13. Point P3 is the contact point between the heel spring and the ground 28. FIG. 3 depicts the typical angle of the heel spring with the ground at the instant of first foot contact during walking. In FIG. 4, the same view is sketched except the angle between the heel spring and the ground 28 is reduced as would be the case during running. This reduction in angle causes the point of contact P4 to move towards the fore end of the heel spring, causing the lower bending beam moment arm 14 to become smaller. The magnitude of the minimum radius of curvature in the concave upwards region of lower beam 15 can be altered to change the rate at which the moment arm changes with changes in the angle between the heel spring bottom and the ground 28. When the heel spring is inside a shoe sole, the outsole or tread will be against the bottom surface of the heel spring. Thus, the bottom surface of the shoe will take on the curvature of the bottom surface of the lower bending beam.

The minimum radius of curvature in the concave downwards regions of both beams 15 and 17 should be maximized, and the beams should be symmetric with each other such that the curvature of lower surface 14 of upper beam 17 matches the curvature of the upper surface 16 of lower bending beam 15 to minimize the chances of breakage during use. For a heel spring that is optimized biomechanically and structurally, the minimum radius of curvature in the concave upwards region should be less than the minimum radius of curvature in the concave downwards region for the upper surface of upper bending beam 8, and for the lower surface of lower bending beam 4. However, it is more critical for the lower bending beam's lower surface 4 to have this specific curvature than for the upper beam's upper surface 8.

To summarize, in a preferred embodiment at least one heel spring bending beam should have a curvature in the fore and aft directions having the following properties:

1) a concave upwards region near the aft end of the bending beam;
2) a concave downwards region near the fore end of the bending beam (i.e. around bending beam axis 19); and
3) a minimum radius of curvature in the concave downwards region which is greater than the minimum radius of curvature in the concave upwards region.

In addition, the heel spring coupled region should have a curvature in the fore and aft directions having no change in concavity and being concave upwards.

Figure 5:
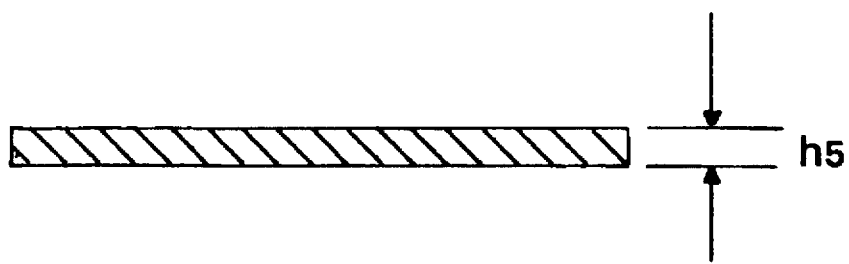
FIG. 5 shows a sectional view taken on the line 5—5 in FIG. 2.
Figure 6:
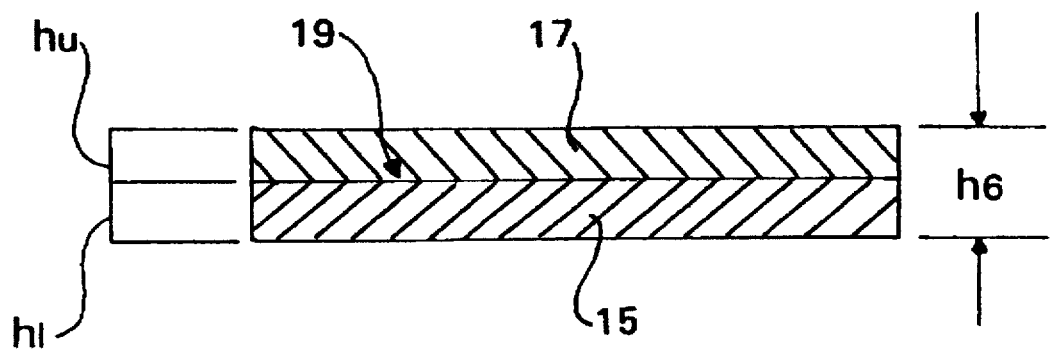
FIG. 6 shows a sectional view taken on the line 6—6 in FIG. 2.
Figure 7:
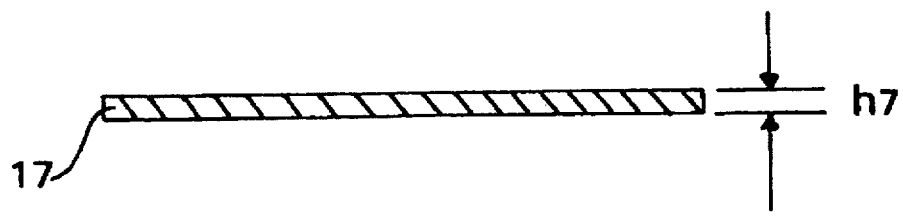
FIG. 7 shows a sectional view taken on the line 7—7 in FIG. 2.

Additional geometric features important to the performance of the heel spring structurally and biomechanically are the tapering of bending beams 15 and 17 and coupled region 21 in height or thickness. The thickness of coupled region 21 is tapered largest at the bending beam axis 19 and smallest at the fore end 11 of the heel spring as sketched in FIG. 2. FIG. 5 shows sectional view 5—5 of FIG. 2 with a thickness of h5, and FIG. 6 shows sectional view 6—6 of FIG. 2 with a thickness of h6. Since coupled region 21 is tapered largest at bending beam axis 19 and smallest at the fore end 11 of the heel spring, h6>h5. Bending beams 15 and 17 are also tapered. FIG. 7 shows sectional view 7—7 of FIG. 2 with a thickness of h7. Since upper beam 17 is tapered, hu>h7 where hu is the thickness of upper bending beam 17 at bending beam axis 19. It is to be understood that lower bending beam 15 is tapered similarly to upper beam 17 as sketched in FIG. 2. The gradual tapers of bending beams 15 and 17 and coupled region 21 make the heel spring optimally light but still structurally durable. Tapering as taught herein does not substantially change beam stiffness.

To summarize, an optimally light bending beam heel spring has the following features:

1) bending beams with tapered thicknesses largest at the bending beam axis and smallest at the aft end of each respective bending beam; and 2) a coupled region with a tapered thickness largest at the bending beam axis and smallest at the fore end of the heel spring.

The length of a bending beam is defined as the distance from the bending beam axis 19 in FIG. 2 to the bending beam's aft end. In FIG. 2, distance lu is the bending beam length for the upper beam 17, and distance ll is the bending beam length for the lower beam 15. The maximum thickness of a bending beam is located at bending beam axis 19 in FIG. 2, or hu for upper beam 17 and hl for lower beam 15 (see FIG. 6). The upper bending beam's dimensionless ratio is defined as the length of the beam divided by its maximum bending beam thickness, or $$\Psi_h = \frac{lu}{hu} \quad (1)$$

The lower bending beam's dimensionless ratio is defined as the length of the beam divided by its maximum bending beam thickness, or $$\Psi_h = \frac{ll}{hl} \quad (2)$$

Experiments were performed in which the bending beam dimensionless ratios (both upper and lower beams) were varied in heel spring prototypes and tested for biomechanical performance. The heel spring prototypes were inserted into the soles of running shoes and tested for shoe cushioning, stability, and economy at running speeds around 4 meters/second. Running shoe biomechanical performance was most significantly increased in the prototype heel springs with bending beam dimensionless ratios numerically between 18 and 35. A preferred range is between 20 and 30. For most runners, the most preferred bending beam dimensionless ratios fell between 22 and 28.

Several heel spring material systems including carbon fiber composite and fiberglass were considered during this investigation. Although, as will be appreciated by those skilled in the art, the dimensionless ratio varies with the type of material used, the above ranges are suitable for the materials tested and are applicable to different foot sizes. The preferred dimensionless ratio for carbon fiber composite systems is between about 22 and about 28.

Figure 8A:
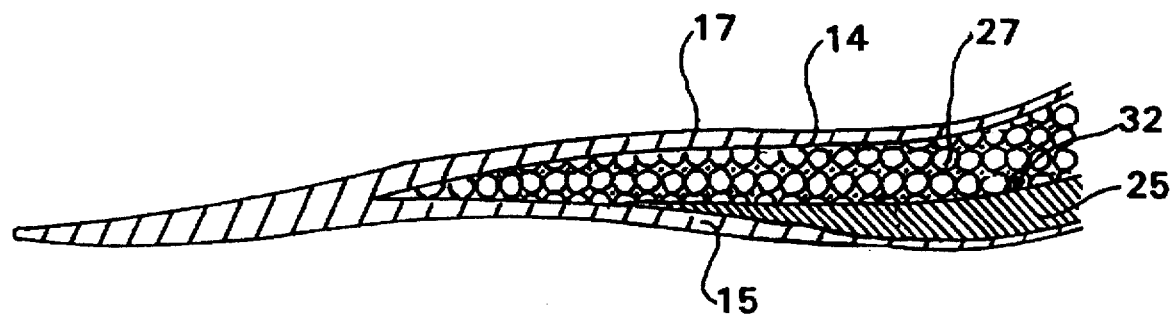
FIG. 8 shows a sectional view taken on the line 2—2 in FIG. 1 with (SA) a stiffening wedge and a bumper or a stop inserted between the bending beams and (SB) a continuous coupled region.

FIG. 8A shows the same heel spring cross sectional view as FIG. 2 with a stiffening wedge 27 and a bumper or a stop 25 between bending beams 15 and 17. Stiffening wedge 27 is an inflatable air bag or a springy material or the like designed to increase the heel spring stiffness for different body weights. Bumper or stop 25 is a hard material designed to stop bending beams 15 and 17 from compressing completely together to minimize the chance of bending beam breakage during use. As will be appreciated by those skilled in the art, bending beam 15 and stop 25 may be all one piece, and the concavity of the bottom surface of the concave upward region of bending beam 15 can be adjusted to match the upper surface of stop 25.

Figure 8B:
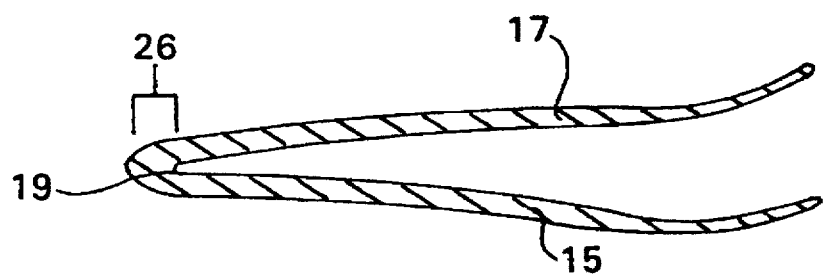

FIG. 8B shows the same heel spring cross sectional view as FIG. 2 except with a modified coupled region. Coupled region 26 and bending beam axis 24 are formed by extending the material of the upper bending beam through to the lower bending beam, forming a non-zero radius of curvature at bending beam axis 24. If the heel spring were made from a composite material, the fibers in the top bending beam would run continuously through to the lower bending beam. This coupled region design is attractive from a manufacturing cost perspective and can perform adequately biomechanically and structurally if the bending beams are designed as described herein. Other coupled region designs include gluing or clamping the upper and lower bending beams together throughout the coupled region. In all these coupled region designs, the region should be tapered largest at the bending beam axis and smallest at the fore end of the heel spring to achieve an optimally light structure.

Figure 9:
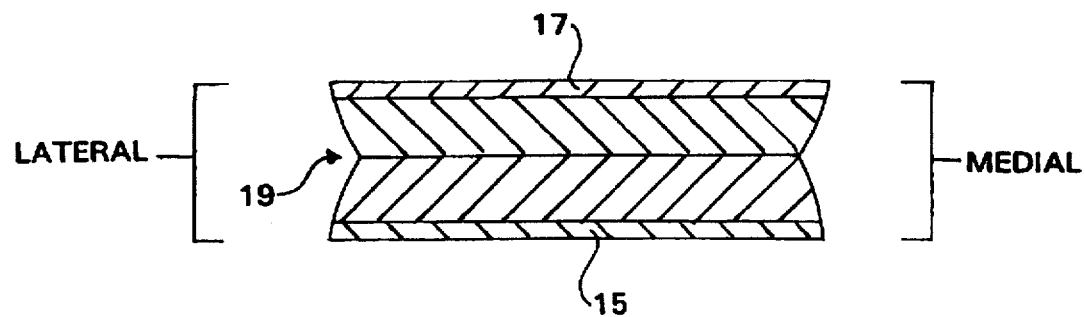
FIG. 9 shows a sectional view taken on the line 9—9 in FIG. 1.

FIG. 9 shows the sectional view 9—9 of FIG. 1. This heel spring is to be used with the left foot. Upper and lower bending beams 17 and 15 are shown, respectively, along with bending beam axis 19 and the heel spring's medial and lateral sides.

Figure 10:
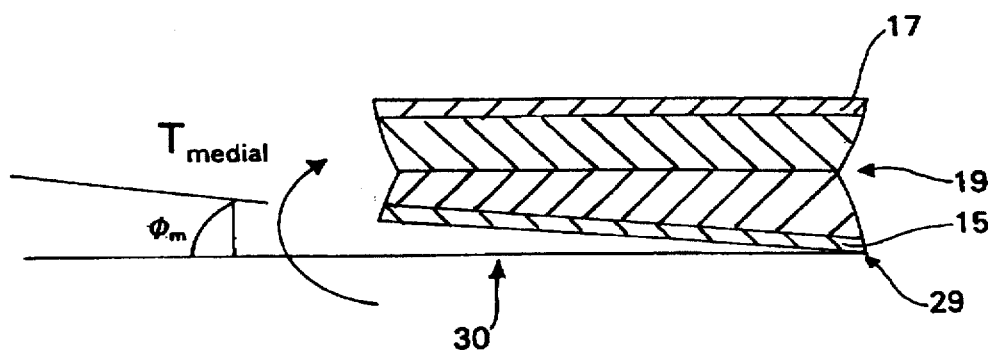
FIG. 10 shows a sectional view taken on the line 9—9 in FIG. 1 with the lower bending beam twisted toward the medial spring side.

FIG. 10 shows the same view as in FIG. 9 except with the lower bending beam twisted toward the medial spring side. A torque $T_{medial}$, acting about an axis passing through point 29 in FIG. 10 (the medial aft corner of the lower beam) and perpendicular to the flat page, twists the lower bending beam 15 towards the heel spring's medial side. Point 29 in FIG. 10 and coupled region 21 in FIG. 2 are both rigidly fixed in space so that the entire spring does not translate when torque $T_{medial}$, is applied. The required torque needed to twist the lower bending beam up at an angle $\phi_m$, divided by that deflection angle $\phi_m$, will be referred to as the medial torsional stiffness $K_{medial}$.

Figure 11:
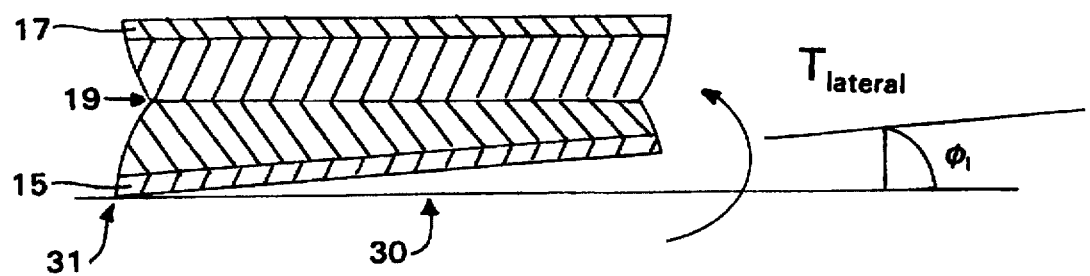
FIG. 11 shows a sectional view taken on the line 9—9 in FIG. 1 with the lower bending beam twisted toward the lateral spring side.

FIG. 11 shows the same view as in FIG. 9 except this time with the lower bending beam twisted toward the lateral spring side. A torque $T_{lateral}$, acting about an axis passing through point 31 in FIG. 11 (the lateral aft corner of the lower beam) and perpendicular to the flat page, twists the lower bending beam 15 towards the heel spring's lateral side. Once again, point 31 in FIG. 11 and coupled region 21 in FIG. 2 are both rigidly fixed in space so that the entire spring does not translate when torque Tlateral is applied. The required torque needed to twist the lower bending beam up at an angle $\phi$1, divided by that deflection angle $\phi_1$, will be referred to as the lateral torsional stiffness $K_{lateral}$.

The torsional stiffness ratio is defined as the lateral torsional stiffness divided by the medial torsional stiffness, $$\Gamma = \frac{K_{lateral}}{K_{medial}} \quad (3)$$

Experiments were performed in which the torsional stiffness ratio was varied in heel spring prototypes and tested for biomechanical performance. The heel spring prototypes were inserted into the soles of running shoes and tested for shoe cushioning and stability at running speeds around 4 meters/second. Shoe cushioning was increased and foot/ankle pronation was decreased most significantly in the prototype heel spring with a torsional stiffness ratio numerically greater than or equal to one. For most runners, the optimal torsional stiffness ratio was between one and ten.

In a preferred embodiment of this invention in which the heel spring is formed from a composite material, the torsional stiffness ratio may be varied by varying the degree of fiber rotation in the bending beams as is known to the art.

The heel spring can be permanently glued into the sole of a shoe, or the spring could be a part of a modular shoe system where the heel spring snaps into and out of a shoe sole. Used as a midsole component, the heel spring would be inserted between the outsole (tread) and the insole upon which the foot directly rests. In addition, the heel spring can be attached to the bottom of a conventional shoe using straps or the like, or to the bottom of an orthotic brace shoe. Still further, the heel spring could be used as part of a prosthetic foot with the spring placed inside a cosmetic foot cover.

It should be understood that the bending beam heel spring as specifically described herein could be altered without deviating from its fundamental nature. For example, the lower and/or upper bending beams 15 and 17 respectively, could be cut down the heel center line from the aft end 13 to the coupled region 21 to form four bending beams, two upper beams and two lower beams. Still further, additional elements may include a heel cup and an arch support built into the heel spring itself. Still further, a material or air wedge could be used between the upper and lower heel spring bending beams to increase heel spring stiffness for different body weights as shown in FIG. 8A.

Figure 12:
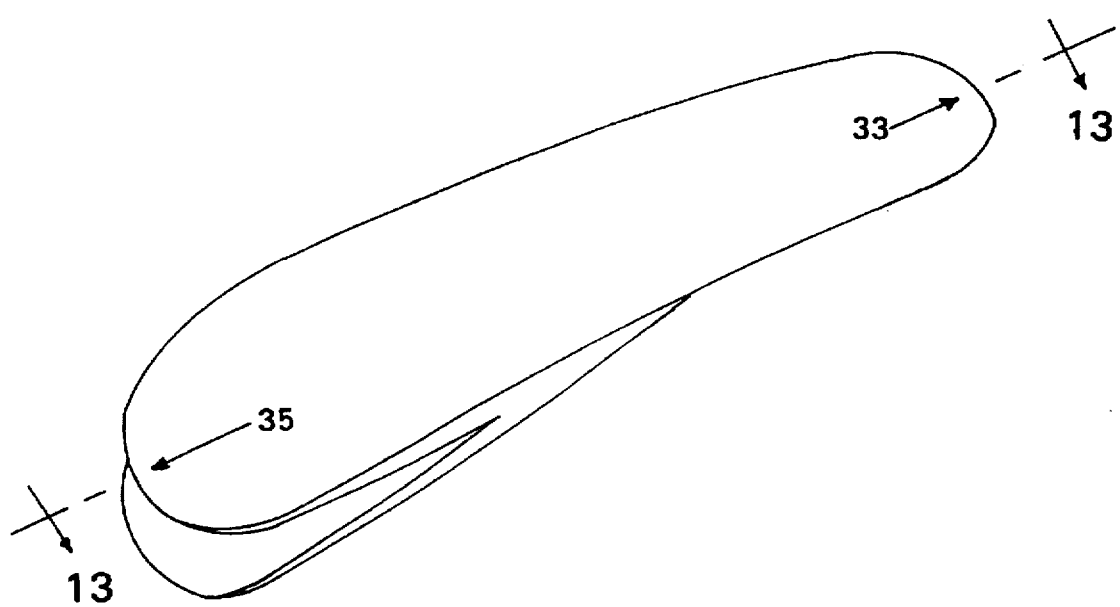
FIG. 12 is a perspective view of a coupled two spring sole system.
Figure 13:
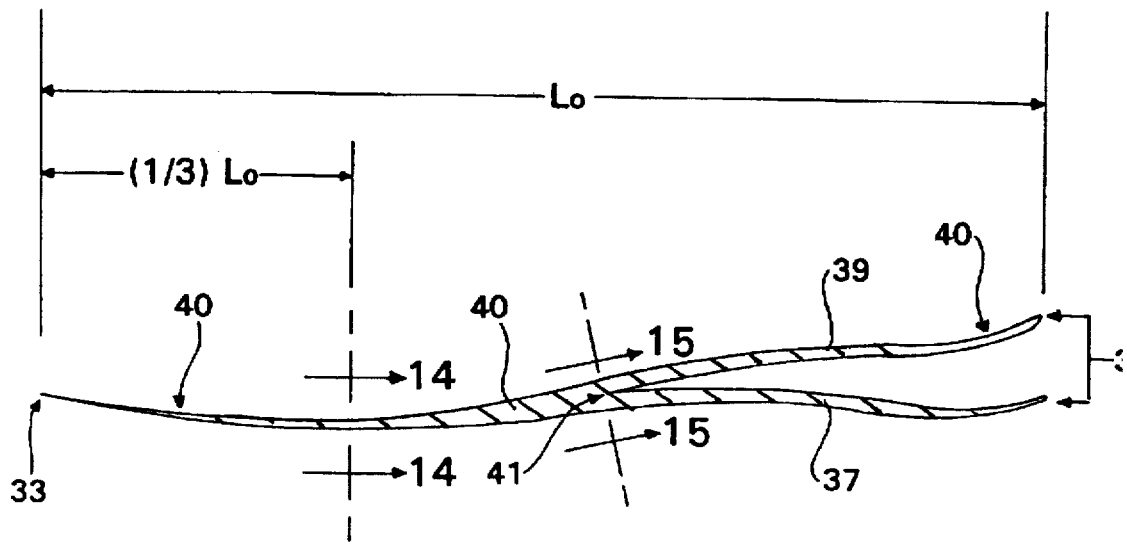
FIG. 13 shows a sectional view taken on the line 13—13 in FIG. 12.

The second embodiment of this invention is a two coupled spring sole system. In FIG. 12, a perspective view of a coupled two spring sole system is sketched. In FIG. 13, the sagittal plane cross sectional view (line 13—13 in FIG. 12) taken through the approximate sole system center line is shown. The sole system has a fore end 33 and an aft end 35. Relative to the foot of the shoe user, the sole system's aft end 35 would be closer to the user's heel than the sole system's fore end 33, and the sole system's fore end 33 would be closer to the user's toes than the sole system's aft end 35. Two springs form the sole system: a bending beam heel spring formed by upper beam 39 and lower beam 37; and a sole spring 40 composed of a fore end extending forward from the heel spring and an aft end composed of the upper bending beam 39 of the heel spring. As the heel spring is compressed, bending beams 39 and 37 bend towards each other and store energy. Once again, the transverse axis where the bending beams come together will be referred to as the bending beam axis 41. The sole spring 40, extending from the fore end 33 of the sole system to its aft end 35, is coupled to the heel spring. In this description, the upper bending beam 39 is shared by the sole spring 40 and the heel spring.

The design details of the bending beam heel spring are preferably as described earlier in the heel spring section of this document.

Figure 16:
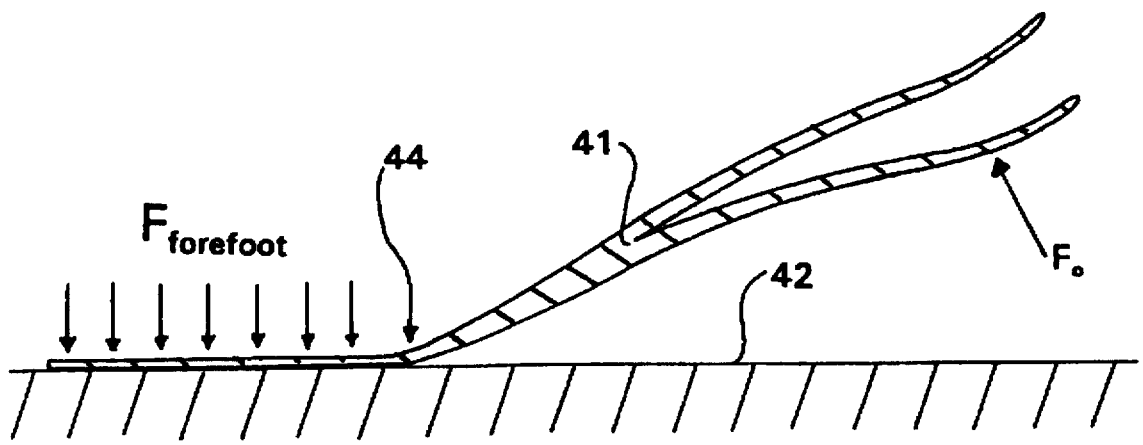
FIG. 16 shows the two coupled spring sole system with the sole spring compressed at the sole spring axis.

The sole spring 40 is a bending beam with a transverse bending axis located approximately ⅔ of the sole system length Lo from its aft end 35 (see FIG. 13). This bending axis will be referred to as the sole spring axis. In FIG. 13, the sole spring axis is located at the sectional line 14—14. When the shoe user's foot is attached to the sole system, the sole spring 40 bends about this axis and stores energy when the foot flexes about the metatarsal-phalangeal joints commonly referred to as the ball of the foot joint. In FIG. 16, the two coupled spring sole system is sketched with the sole spring compressed at the sole spring axis 44. Forefoot forces $F_{forefoot}$ press the front portion of the sole spring against rigid surface 42. When a force $F_0$ acts near the aft end 35 of the sole system, the sole spring bends at the sole spring axis 44. The bending beam axis 41 is located between the aft end 35 of the sole system and the sole spring axis 44.

During a heel-toe walking or running sequence, the heel spring compresses and stores energy as the heel of the shoe or prosthesis strikes the ground. In a shoe sole, the compressed heel spring then exerts a force underneath the user's heel, thrusting the heel upward as the foot flexes about the metatarsal-phalangeal joints. During this flexion period, the sole spring compresses about the sole spring axis and stores energy. The spring exerts a torque about the metatarsal-phalangeal joints, enhancing toe-off propulsion. In a prosthetic foot, the expansion of the heel spring enables the amputee to bend the sole spring about its sole spring axis. The sole spring energy then gives the amputee toe-off propulsion. Thus, effectively the elastic energy stored at impact is transferred to the sole spring. Elastic energy is stored in the sole system early in the foot contact period and then released to the user late in the period to enhance or create toe-off propulsion. This method of delivering the heel spring energy to the walker or runner is believed to be optimal.

Figure 14:
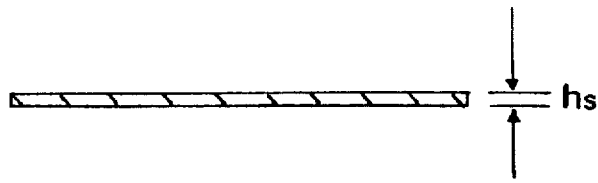
FIG. 14 shows a sectional view taken on the line 14—14 in FIG. 13.
Figure 15:
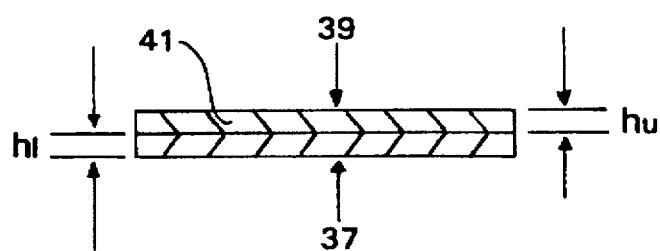
FIG. 15 shows a sectional view taken on the line 15—15 in FIG. 13.

For the heel spring energy to be effectively transferred to the sole spring, the relationship between the stiffnesses of the upper and lower bending beams to the stiffness of the sole spring 40 at the sole spring axis 44 is critical. Through biomechanical experimentation, it has been found that the maximum bending beam height or thickness at the bending beam axis 41 divided by the height or thickness of the sole spring 40 at the sole spring axis 44 has to be within a particular numerical range for the heel spring energy to be effectively transferred to the sole spring. This dimensionless number will be called the heel spring/sole spring thickness ratio. For the upper bending beam 39, this ratio is:

$$\Xi_h = \frac{hu}{hs} \quad (4)$$

where hu is the maximal thickness of the upper bending beam 39 (see FIG. 15) and hs is the thickness of the sole spring 40 at the sole spring axis 44. The thickness hs is sketched in FIG. 14, sectional view 14—14 of FIG. 13. For the lower bending beam 37, the ratio is:

$$\Xi_h = \frac{hl}{hs} \quad (5)$$

where hl is the maximal thickness of the lower bending beam 37 (see FIG. 15).

Experiments were performed in which the heel spring/sole spring thickness ratios (both upper and lower beams) were varied in spring prototypes and tested for biomechanical performance. The heel spring energy was most effectively transferred to the sole spring with heel spring/sole spring thickness ratios numerically greater than one and preferably not more than about twenty. For most runners, the optimal heel spring/sole spring thickness ratios fell between 2 and 10.

The two coupled spring sole system could be permanently glued into the sole of a shoe, or the spring system could be a part of a modular shoe system where the sole system snaps into or out of a shoe sole. In addition, the sole system could be attached to the bottom of a conventional shoe using straps or the like, or to the bottom of an orthotic brace shoe. Still further, the sole system could be used as part of a prosthetic foot with the spring placed inside a cosmetic foot cover.

It should be understood that the two coupled spring sole system as specifically described herein could be altered without deviating from its fundamental nature. For example, additional upper and lower bending beams could be used in the heel spring, and different coupled region designs could be employed as was described earlier. The sole spring could be made separately from the heel spring and positioned relative to the heel spring by a clamp or by the shoe casing such that the sole spring axis is beneath the ball of the foot, and that the bending beam axis is between the sole spring axis and the aft end of the sole system. The sole spring need not extend to the aft end of the heel spring, i.e., to the aft end of the sole system. Still further, a material or air wedge could be used between the upper and lower heel spring bending beams to increase heel spring stiffness for different body weights. Further, the heel spring may comprise at least one spring type known to the art other than disclosed herein, including an oyster spring, a helical spring or saucer spring as described in U.S. Ser. No. 08/222,718, incorporated herein by reference.

The third embodiment of this invention is a forefoot spring. During a walking or running sequence, a forefoot spring begins to compress and store energy as the forefoot of the shoe or prosthetic foot strikes the ground. During this period, a forefoot spring can reduce impact forces and store energy if designed properly.

Figure 17:
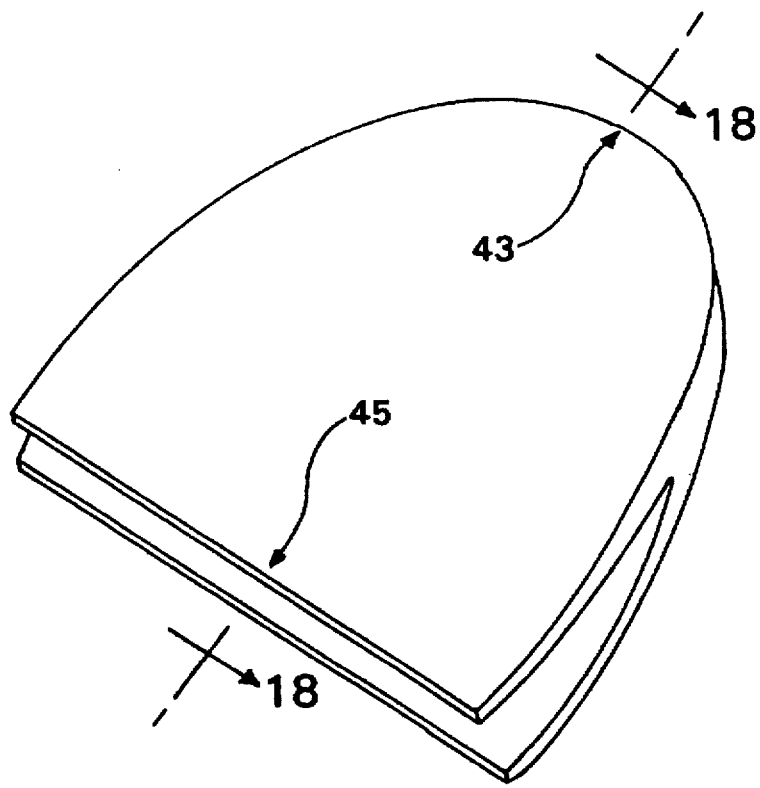
FIG. 17 is a perspective view of a bending beam forefoot spring.
Figure 18:
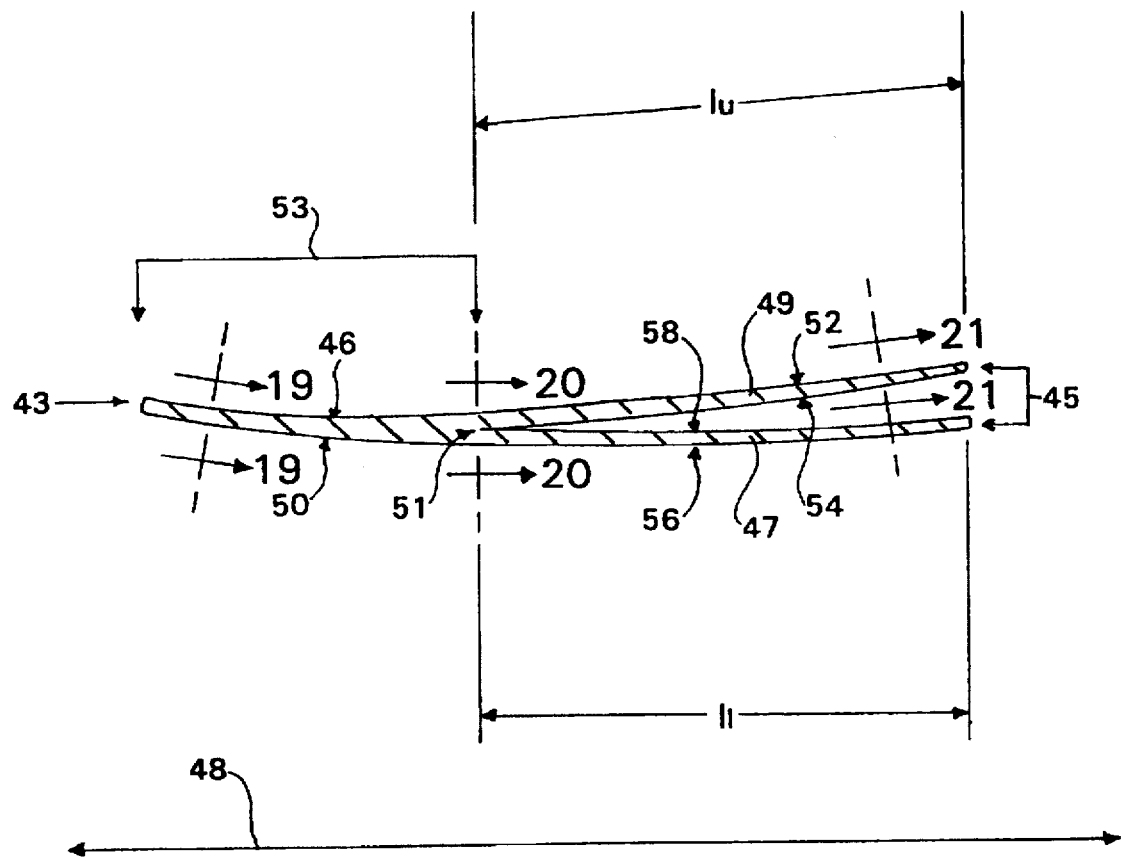
FIG. 18 shows a sectional view taken on the line 18—18 in FIG. 17.

In FIG. 17, a perspective view of an optimized forefoot spring is sketched. In FIG. 18, the sagittal plane cross sectional view (line 18—18 in FIG. 17) taken through the approximate forefoot spring center line is shown. The spring has a fore end 43 and an aft end 45. Relative to the foot of the shoe user, the spring's aft end 45 would be closer to the user's heel than the spring's fore end 43, and the spring's fore end 43 would be closer to the user's toes than the spring's aft end 45. Two bending beams, an upper beam 49 and a lower beam 47, form the spring. When the forefoot spring is compressed, the bending beams 47 and 49 bend towards each other and store energy. The transverse axis where the bending beams come together will be referred to as the bending beam axis 51. The bending beams 47 and 49 are coupled together at and near the fore end 43 of the forefoot spring. The region where the beams are adjoined will be referred to as the coupled region 53.

The geometries of the bending beam forefoot spring are critical to the spring's performance structurally and biomechanically. The first feature of interest is the curvature of the bending beams 47 and 49 and the coupled region 53 in the fore and aft directions defined by axis 48 in FIG. 18. In FIG. 18, the bending beams 47 and 49 and the coupled region 53 do not change concavity and are concave-upwards. The top surface of coupled region 53 and upper beam 49 form a continuous concave-upwards line in the fore and aft directions, and the bottom surface of coupled region 53 and lower beam 47 form a continuous concave-upwards line in the fore and aft directions.

Bending beam and coupled region curvature is critical to the performance of the forefoot spring for several reasons. The shoe user's forefoot fits nicely onto the concave upwards curvature of the upper beam's and the coupled region's upper surfaces 52 and 46 respectively. The concave upwards curvature of the lower surface of coupled region 50 and lower beam 56 is not as critical as the upper surface of upper beam 52 and coupled region 46. However, as sketched in FIG. 18, the curvature of this lower surface in the fore and aft directions 48 should be concave upwards optimally. This lower surface curvature to the forefoot spring enables the spring to roll against the running surface during use. In addition, the upper and lower bending beams should be symmetric with each other, such that the curvature of the upper surface of the lower beam 58 matches that of the lower surface of the upper beam 54, to minimize the chances of the spring breaking during use.

To summarize, in a preferred embodiment at least one forefoot spring bending beam should have a curvature in the fore and aft directions having no change in concavity and be concave upwards.

In addition, the forefoot spring coupled region should have a curvature in the fore and aft directions having no change in concavity and be concave upwards.

Figure 19:
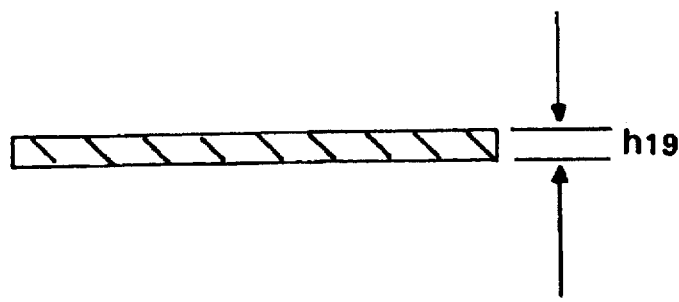
FIG. 19 shows a sectional view taken on the line 19—19 in FIG. 18.
Figure 20:
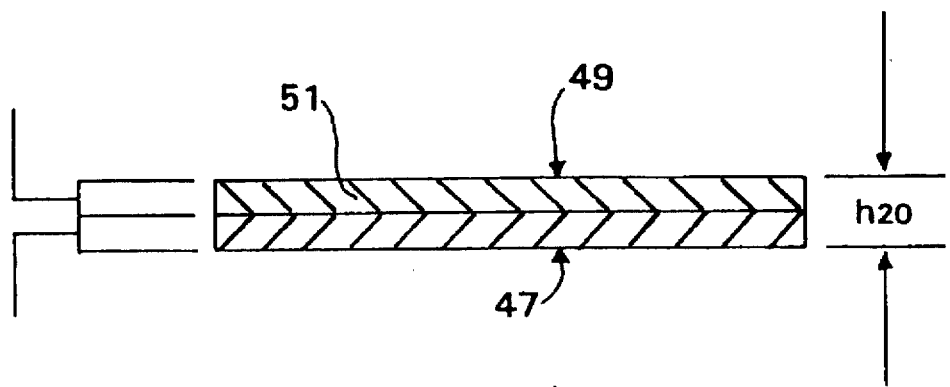
FIG. 20 shows a sectional view taken on the line 20—20 in FIG. 18.
Figure 21:
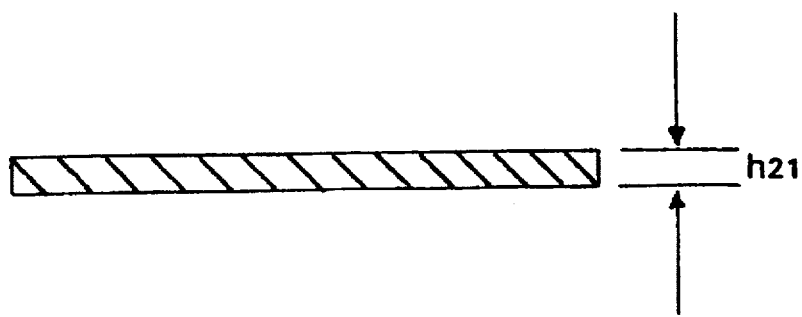
FIG. 21 shows a sectional view taken on the line 21—21 in FIG. 18.

Additional geometric features important to the performance of the heel spring structurally and biomechanically are the tapering of bending beams 47 and 49 and coupled region 53 in height or thickness. The thickness of coupled region 53 is tapered largest at the bending beam axis 51 and smallest at the fore end 43 of the forefoot spring as sketched in FIG. 18. FIG. 19 shows sectional view 19—19 of FIG. 18 with a thickness of h19, and FIG. 20 shows sectional view 20—20 of FIG. 18 with a thickness of h20. Since coupled region 53 is tapered largest at bending beam axis 51 and smallest at the fore end 43 of the forefoot spring, h20>h19. Bending beams 47 and 49 are also tapered. FIG. 21 shows sectional view 21—21 of FIG. 18 with a thickness of h21. Since upper beam 49 is tapered, hu>h21 where hu is the thickness of upper bending beam 49 at bending beam axis 51 (see FIG. 20). It is to be understood that lower bending beam 47 is tapered similarly to upper beam 49 as sketched in FIG. 18. The gradual tapers of bending beams 47 and 49 and coupled region 53 make the forefoot spring optimally light but still structurally durable.

To summarize, an optimally light bending beam forefoot spring has the following features:

1) bending beams with tapered thicknesses largest at the bending beam axis and smallest at the aft end of each respective bending beam; and 2) a coupled region with a tapered thickness largest at the bending beam axis and smallest at the fore end of the forefoot spring.

The length of a bending beam is defined as the distance from the bending beam axis 51 in FIG. 18 to the bending beam's aft end. In FIG. 18, distance lu is the bending beam length for the upper beam 49, and distance ll is the bending beam length for the lower beam 47. The maximum height or thickness of a bending beam is located at the bending beam axis 51 in FIG. 18, or hu for upper beam 49 and hl for lower beam 47 (see FIG. 20). The upper bending beam's dimensionless ratio is defined as the length of the beam divided by its maximum bending beam thickness, or $$\Psi_f = \frac{lu}{hu} \quad (6)$$

The lower bending beam's dimensionless ratio is defined as the length of the beam divided by its maximum bending beam thickness, or $$\Psi_f = \frac{ll}{hl} \quad (7)$$

Experiments were performed in which the bending beam dimensionless ratios (both upper and lower beams) were varied in forefoot spring prototypes and tested for biomechanical performance. The forefoot spring prototypes were inserted into the soles of running shoes and tested for shoe cushioning, stability, and economy at running speeds around 4 meters/second. Running shoe biomechanical performance was most significantly increased in the prototype forefoot springs with bending beam dimensionless ratios numerically between 18 and 35. Preferably this ratio is between 20 and 30. For most runners, the most preferred bending beam dimensionless ratios fell between 22 and 28.

The forefoot spring could be permanently glued into the sole of a shoe, or the spring could be a part of a modular shoe system where the forefoot spring snaps into or out of a shoe sole. In addition, the forefoot spring could be attached to the bottom of a conventional shoe using straps or the like, or to the bottom of an orthotic brace shoe. Still further, the forefoot spring could be used as part of a prosthetic foot with the forefoot spring placed inside a cosmetic foot cover.

It should be understood that the forefoot spring as specifically described herein could be altered without deviating from its fundamental nature. As with the heel spring, additional upper and lower bending beams could be used. For example, the lower and/or upper bending beams 47 and 49 respectively, could be cut down the forefoot center line from the aft end 45 to the coupled region 53 to form four bending beams, two upper beams and two lower beams. In addition, different coupled region designs could be employed as was described in the heel spring section. Still further, a material or air wedge could be used between the upper and lower bending beams to increase forefoot spring stiffness for different body weights.

Figure 22:
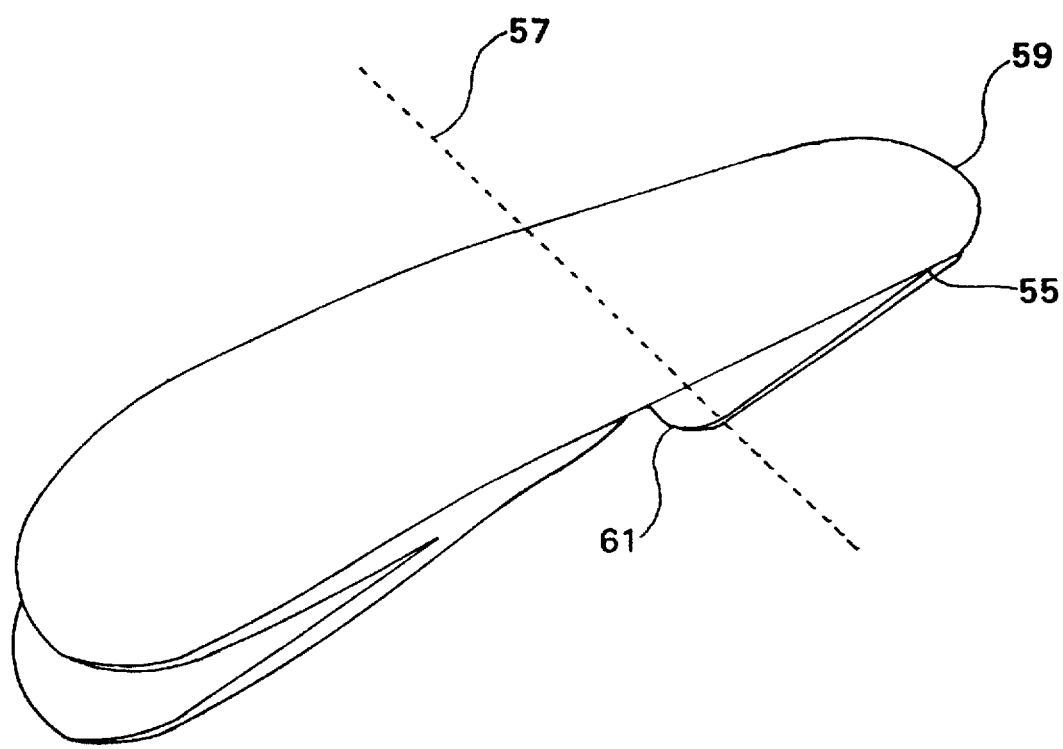
FIG. 22 shows a perspective view of a three coupled spring sole system.

The fourth embodiment of this invention comprises a three coupled spring sole system. An improvement in biomechanical performance can be achieved over the two coupled spring sole system described earlier by adding a forefoot spring to the system of springs. A perspective view of the three coupled spring sole system is sketched in FIG. 22. The details of the bending beam heel, sole and forefoot spring designs are preferably as described earlier in the heel and forefoot spring sections of this document. The forefoot spring is coupled to the sole spring such that the forefoot spring's bending beam axis 55 is located between the sole spring axis 57 and the fore end 59 of the sole system. The aft end 61 of the forefoot spring is located approximately under the sole spring axis 57. The heel spring/sole spring thickness ratio discussed earlier should not change when the forefoot spring is added to the two coupled spring sole system; the stiffness of the sole spring for bending about the sole spring axis 57 should not increased when the forefoot spring is coupled to the sole spring. Several coupling means could be used to achieve this objective. For example, the forefoot spring could be glued or clamped onto just the fore end 59 of the sole system, or the forefoot spring could be placed inside a shoe casing, holding the spring in the correct position without increasing the sole spring bending stiffness. Thus, here again, the word "coupled" does not necessarily mean rigidly attached or even touching, but rather "placed in cooperative relationship with" so that force from the release of one spring will push on the coupled spring member.

When the heel of a shoe or foot prosthesis strikes the ground during a heel-toe walking or running sequence, the heel spring compresses and stores energy. After heel impact, the forefoot of the shoe or foot prosthesis strikes the ground and the forefoot spring begins to compress. The forefoot spring continues to compress as the center of pressure moves into the forefoot region. The shifting of weight from the heel to the forefoot enables the heel spring to release its energy, propelling the heel upward away from the ground. The heel spring energy helps to bend the sole spring as discussed earlier. After this bending period, forefoot lift-off begins. The forefoot spring begins to release its energy pushing on the bottom of the forefoot. During the same period, the sole spring releases its energy creating or enhancing toe-off propulsion. Thus, during this final period, both the sole spring and the forefoot spring release energy propelling the walker or runner upwards and forwards.

The coupled three spring sole system could be permanently glued into the sole of a shoe, or the sole system could be part of a modular shoe where the springs snap into or out of a shoe sole. In addition, the springs could be attached to the bottom of a conventional shoe using straps or the like, or to the bottom of an orthotic brace shoe. Still further, the springs could be used as part of a prosthetic foot with the springs placed inside a cosmetic foot cover.

It should be understood that the three coupled spring sole system as specifically described herein could be altered without deviating from its fundamental nature. For example, additional upper and lower bending beams could be used in the heel and forefoot springs, and different coupled region designs could be employed as was described earlier. Still further, a material or air wedge could be used between the upper and lower heel and forefoot spring bending beams to increase heel and forefoot spring stiffnesses for different body weights. Further, the heel spring or forefoot spring may comprise at least one spring type known to the art other than disclosed herein, including an oyster spring, a helical spring or a saucer spring as described in U.S. Ser. No. 08/222,718 incorporated herein by reference.

It is therefore to be understood that within the scope of the appended claims, the invention may be practiced in ways other than as specifically described herein.

We claim:

1. A sole system which comprises:

a heel spring formed by upper and lower bending beams attached at a single coupled region;

wherein each of said bending beams has a fore end and an aft end, a medial edge and a lateral edge, and an upper surface and a lower surface;

wherein said heel spring has a fore end and an aft end;

wherein said coupled region has a fore end and an aft end;

wherein said bending beams are rigidly attached within said coupled region;

wherein said coupled region is the only region of said heel spring in which a force exerted on one bending beam will influence the other bending beam;

wherein said heel spring has a single bending beam axis at said coupled region's aft end where the upper surface of the lower bending beam adjoins the lower surface of the upper bending beam along a continuous straight line from the lateral to the medial edges of said bending beams;

wherein each of said bending beams in use is capable of bending toward the other and storing energy in the region between said bending beam axis and said bending beam's aft end;

wherein said bending beams are made of a material such that said spring has an energy return of at least 70%; and wherein at least one of said bending beam surfaces has a concave upward region on its aft end and a concave downward region on its fore end; and wherein a minimum radius of curvature in said concave upward region is less than a minimum radius of curvature in said concave downward region.

2. The sole system of claim 1 wherein said surface having said concave regions is the lower surface of the lower bending beam.

3. The sole system of claim 1 wherein said coupled region has an upper and lower surface, at least one of which said surfaces is concave upwards.

4. The sole system of claim 1 wherein at least one bending beam has a tapered thickness largest at the bending beam axis and smallest at the aft end of said bending beam.

* * * * *